(12) United States Patent
Kang (10) Patent No.: US 12,285,313 B2
(45) Date of Patent: Apr. 29, 2025

(54) DENTAL DUAL-STRUCTURED MEMBRANE AND METHOD FOR MANUFACTURING DENTAL DUAL-STRUCTURED MEMBRANE

(71) Applicant: PURGO BIOLOGICS INC., Seongnam-si (KR)

(72) Inventor: Ho Chang Kang, Seongnam-si (KR)

(73) Assignee: PURGO BIOLOGICS INC. (KR)

( * ) Notice: Subject to any disclaimer, the term of this patent is extended or adjusted under 35 U.S.C. 154(b) by 1128 days.

(21) Appl. No.: 17/264,795

(22) PCT Filed: Jun. 24, 2019

(86) PCT No.: PCT/KR2019/007600
§ 371 (c)(1),
(2) Date: Jan. 29, 2021

(87) PCT Pub. No.: WO2020/027439
PCT Pub. Date: Feb. 6, 2020

(65) Prior Publication Data
US 2021/0290344 A1    Sep. 23, 2021

(30) Foreign Application Priority Data
Jul. 31, 2018 (KR) .................... 10-2018-0089299

(51) Int. Cl.
| | |
|---|---|
| A61C 8/02 | (2006.01) |
| A61L 27/24 | (2006.01) |
| A61L 31/04 | (2006.01) |
| A61L 31/14 | (2006.01) |
| C08J 3/24 | (2006.01) |

(52) U.S. Cl.
CPC ............ *A61C 8/0006* (2013.01); *A61L 27/24* (2013.01); *A61L 31/044* (2013.01); *A61L 31/148* (2013.01); *C08J 3/24* (2013.01); *A61L 2430/12* (2013.01); *C08J 2300/16* (2013.01)

(58) Field of Classification Search
None
See application file for complete search history.

(56) References Cited

U.S. PATENT DOCUMENTS 5,776,193 A  *  7/1998  Kwan ................ A61L 24/0036
                                           623/23.61
2016/0206784 A1    7/2016  Jessop et al.

FOREIGN PATENT DOCUMENTS

| CN | 106345424 A | | 1/2017 |
|---|---|---|---|
| CN | 107206125 A | | 9/2017 |
| KR | 20130101872 A | | 9/2013 |
| KR | 20140059421 A | | 5/2014 |
| KR | 20150134193 | * | 5/2014 |
| KR | 20150134193 A | * | 5/2014 |
| KR | 20160091195 A | | 8/2016 |
| KR | 20180078624 | * | 12/2016 |
| KR | 20180078624 A | * | 12/2016 |
| KR | 101731057 B1 | | 4/2017 |
| KR | 101938263 B1 | | 1/2019 |
| WO | WO2016195152 | * | 6/2015 |
| WO | WO2016195152 A | * | 6/2015 |
| WO | 2018107121 A2 | | 6/2018 |

OTHER PUBLICATIONS

International Search Report for PCT/KR2019/007600 mailed Oct. 10, 2019.
European Extended Search Report for Application No. 19843680.0, mailed Aug. 9, 2021.

* cited by examiner

*Primary Examiner* — Celeste A Roney
(74) *Attorney, Agent, or Firm* — Renaissance IP Law Group LLP

(57) ABSTRACT

Provided is a dental dual-structured membrane. The dental dual-structured membrane according to an embodiment of the present inventive concept includes a shielding portion for shielding a bone grafting material and an alveolar bone from the outside to prevent infiltration of other tissue cells, and an insertion and fixing portion connected to the shielding portion and inserted between a gum and the alveolar bone to fix the shielding portion, in which the insertion and fixing portion has a higher tensile strength than the shielding portion.

16 Claims, 8 Drawing Sheets

DENTAL DUAL-STRUCTURED MEMBRANE AND METHOD FOR MANUFACTURING DENTAL DUAL-STRUCTURED MEMBRANE

TECHNICAL FIELD

The present inventive concept relates to a dental membrane, and more particularly, to a dental dual-structured membrane, which may be very easily, simply, and accurately fixed at a desired position and may be prevented from moving away from the fixed position, and a method for manufacturing a dental dual-structured membrane.

BACKGROUND ART

Dental membranes refer to membranes for regeneration of an alveolar bone, which are used to regenerate a hard tissue (bone) such as an alveolar bone, and the like. In orthodontic procedures or implant procedures, when the regeneration of an alveolar bone, for example, an alveolar bone is thin, damaged or lost, and the like, is needed, dental membranes are used for bone regeneration or bone grafting.

In detail, in orthodontic procedures or implant procedures, when bone quality is poor or the amount of bone is insufficient, or when an alveolar bone is destroyed or lost due to periodontitis, an implant may not be placed immediately, so a treatment to increase the alveolar bone is necessary. As such, when osteogenesis (bone composition) is necessary, guided bone regeneration (GBR) or bone grafting may be performed.

Dental membranes are used for GBR, and a membrane for GBR (membrane for guided bone regeneration) that optionally regrows cells is used to independently regenerate each tissue during a healing period.

In other words, after a graft surgery of a bone grafting material, the dental membrane prevents bone tissue formation as other tissue cells infiltrate between the bone grafting material and the alveolar bone, and stably guides bone tissue cells.

In the method of using a dental membrane, in general, a rectangular membrane is trimmed into an appropriate shape and attached at a position where bone loss is generated. A dental membrane according to the related art is porous tissues and has a weak tensile strength so that it is difficult to fix the dental membrane at an accurate position, and even when the dental membrane is fixed at a desired position, the dental membrane is often moved away from the fixed position.

To solve the above problems, a screw was used to fix a dental membrane. In this case, as a relatively large area needs to be cut to install a screw, a surgery time may increase and further swellings may be caused by bleeding which makes patients to suffer. Accordingly, it is a problem that both an operator and a patient may feel some pressure on the surgery.

Furthermore, Korean Patent No. 10-1182806 ("Membrane for regeneration of alveolar bone") discloses a membrane for regeneration of an alveolar bone, in which a hole for passing an implant insertion is formed at a center thereof, the membrane has an overall rounded shape, and the implant insertion is installed by passing through a fixing hole of a dental membrane.

However, bone grafting is most performed when it is difficult to install an implant insertion, and is most carried out before the insertion of the implant insertion. Thus, it is a problem that the patent literature case is inappropriate to a surgery method in which an implant surgery is performed after bone grafting

DETAILED DESCRIPTION OF THE INVENTIVE CONCEPT

Technical Problem

The present inventive concept provides a dental dual-structured membrane having a dual-structure, in which at least one portion of a dental membrane has a higher tensile strength than the other portion thereof, thereby being easily, simply, and accurately fixed at a desired position, without using a screw for fixing the dental membrane, and being prevented from moving away from the fixed position, and also provides a method for simply and efficiently manufacturing the dental dual-structured membrane.

Solution to Problem

According to an aspect of the present inventive concept, a dental dual-structured membrane includes a shielding portion for shielding a bone grafting material and an alveolar bone from the outside to prevent infiltration of other tissue cells, and an insertion and fixing portion connected to the shielding portion and inserted between a gum and the alveolar bone to fix the shielding portion, wherein the insertion and fixing portion has a higher tensile strength than the shielding portion.

The insertion and fixing portion may be provided at at least one portion of a circumference of the shielding portion.

The insertion and fixing portions may be arranged to face each other with the shielding portion between and to be connected to the shielding portion.

The shielding portion and the insertion and fixing portion each may include a biodegradable material.

The shielding portion and the insertion and fixing portion may have a difference in tensile strength due to a density difference.

The shielding portion and the insertion and fixing portion may have a difference in tensile strength due to a different molecular structure.

According to another aspect of the present inventive concept, a method for manufacturing a dental dual-structured membrane, the dental dual-structured membrane including a shielding portion in contact with a bone grafting material to prevent infiltration of other tissue cells toward a bone grafting material and an alveolar bone, and an insertion and fixing portion connected to the shielding portion, having a higher tensile strength than the shielding portion, and inserted between a gum and the alveolar bone to fix the shielding portion, the method including a biodegradable polymer providing step of providing a biodegradable polymer, a molding material providing step of providing a molding material including the biodegradable polymer, a molding material input step of inputting the molding material into a sheet type mold to mold the molding material in a form of a sheet, a membrane sheet molding step of molding the molding material input into the sheet type mold in a membrane sheet by drying the molding material, and a membrane sheet compression step of compressing a part of the membrane sheet to provide the insertion and fixing portion having a reinforced tensile strength and the shielding portion that is the other part of the membrane sheet.

The method may further include, after the membrane sheet molding step, cutting the membrane sheet in a predetermined size.

The molding material providing step may include a step of providing a first mixed liquid by adding the biodegradable polymer to an isopropanol aqueous solution and agitating a resultant using a homogenizer, a step of providing a second mixed liquid by agitating the first mixed liquid and distilled water, a step of providing a third mixed liquid by adding a 1% HCl aqueous solution to the second mixed liquid and agitating a resultant, and a step of providing a molding material by removing air bubbles from the third mixed liquid in a vacuum oven under decompression.

The membrane sheet molding step may include a first drying step of providing a first dry sheet by drying, in an oven, a sheet type mold into which the molding material is input, a sheet cleaning step of cleaning the first dry sheet, and a second drying step of molding a cleaned first dry sheet into a membrane sheet by freezing and drying the cleaned first dry sheet at a temperature lower than a predetermined reference temperature.

The sheet cleaning step may include a step of putting the first dry sheet in a tray containing a phosphate buffered saline (PBS) liquid and shaking the tray, and a step of removing the PBS liquid and cleaning the first dry sheet using distilled water until pH reaches 7.0 to 8.0.

The membrane sheet molding step may further include, after the first drying step, an ultraviolet (UV) crosslinking step of providing a crosslinked sheet to reinforce tensile strength by crosslinking of the biodegradable polymer, by irradiating UV light to a predetermined position of the first dry sheet where the insertion and fixing portion is to be provided, and wherein, in the sheet cleaning step, the crosslinked sheet is cleaned.

The molding material may include a shielding portion molding material for forming the shielding portion and an insertion and fixing portion molding material for forming the insertion and fixing portion.

The shielding portion molding material may be provided to include a larger amount of distilled water than the insertion and fixing portion molding material.

In the molding material input step, the shielding portion molding material may be input into one predetermined area of the sheet type mold where the shielding portion is to be formed, and the insertion and fixing portion molding material may be input into another predetermined area of the sheet type mold where the insertion and fixing portion is to be formed.

The biodegradable polymer may include collagen, the collagen including porcine-derived collagen, and the biodegradable polymer providing step may be a collagen providing step of providing the collagen, the collagen providing step may include a pig ligament preprocessing step of preprocessing a pig ligament to obtain collagen from the pig ligament, a collagen dough molding step of molding a preprocesses pig ligament into a collagen dough, a homogenization step of dissolving the collagen dough in a solvent to obtain a homogenized collagen solution, and a collagen filtering step of filtering collagen from a homogenized collagen solution.

Advantageous Effects

According to an embodiment of the present inventive concept, as the dental dual-structured membrane has a dual-structure, in which at least one portion of a dental membrane has a higher tensile strength than the other portion thereof, the dental dual-structure membrane may be easily, simply, and accurately fixed at a desired position, without using a screw for fixing the dental membrane, and may be prevented from moving away from the fixed position.

Furthermore, according to the methods for manufacturing a dental dual-structured membrane according to embodiments of the present inventive concept, a dental dual-structured membrane having a dual-structure in which tensile strength is partially different may be simply and efficiently manufactured.

MODE OF THE INVENTIVE CONCEPT

In order to fully understand the operational advantages of the present inventive concept and the objectives achieved by the implementation of the present inventive concept, the accompanying drawings illustrating preferred embodiments of the present inventive concept and the contents described in the accompanying drawings are referred to.

Hereinafter, the inventive concept will be described in detail by explaining preferred embodiments of the inventive concept with reference to the attached drawings. Like reference numerals in the drawings denote like elements.

Figure 1:
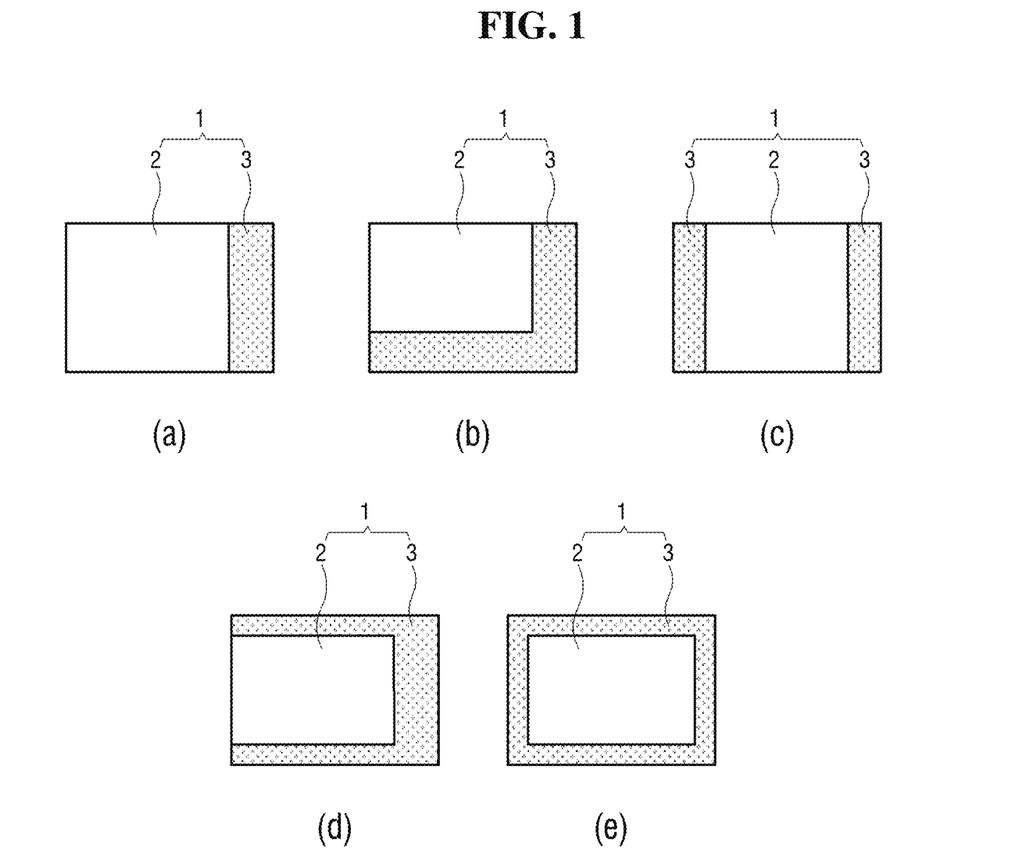
FIG. 1 is a view of various embodiments of a dental dual-structured membrane according to the present inventive concept.
Figure 2:
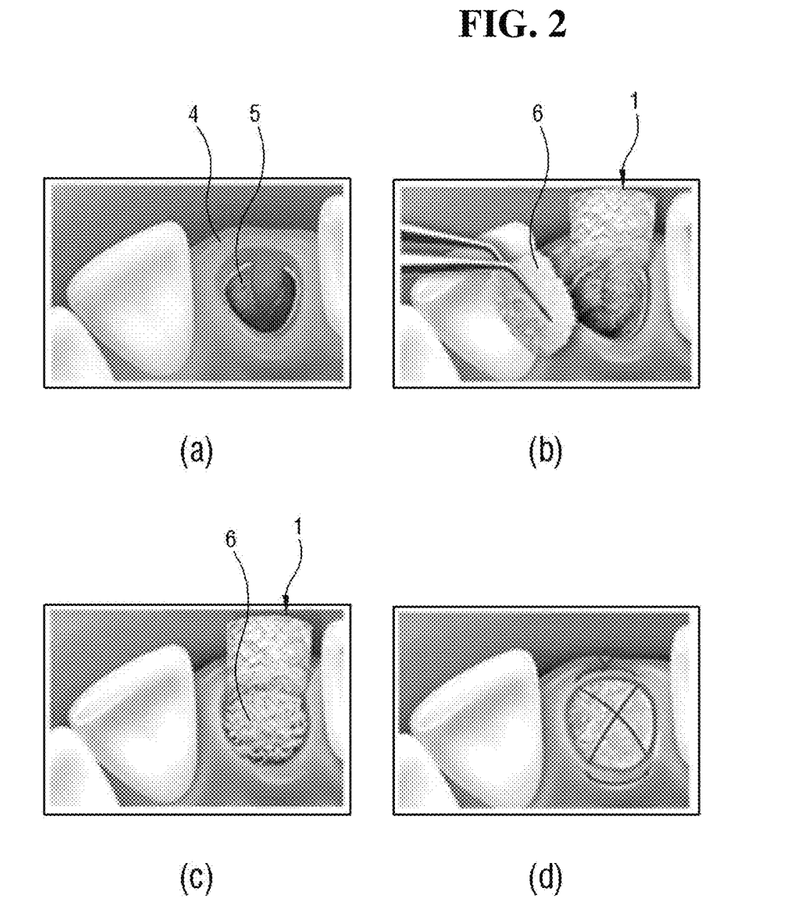
FIG. 2 is a view of a bone grafting surgery procedure using a dental dual-structured membrane according to an embodiment of the present inventive concept.

FIG. 1 is a view of various embodiments of a dental dual-structured membrane according to the present inventive concept. FIG. 2 is a view of a bone grafting surgery procedure using a dental dual-structured membrane according to an embodiment of the present inventive concept.

As illustrated in the drawings, a dental dual-structured membrane 1a according to the present inventive concept is a membrane sheet having a sheet shape and may include a shielding portion 2 and an insertion and fixing portion 3.

The shielding portion 2 is connected to the insertion and fixing portion 3, forming one sheet, and the insertion and fixing portion 3 is manufactured to have a higher tensile strength than the shielding portion 2.

As the dental dual-structured membrane 1 has two portions having tensile strength different from each other, the dental dual-structure membrane 1 may be easily, simply, and accurately fixed at a desired position, without using a screw for fixing the dental membrane, and may be prevented from moving away from the fixed position. Furthermore, the dental dual-structure membrane 1 may be manufactured by a simple and efficient method.

The shape of the dental dual-structured membrane 1 is described with reference to FIG. 1. Although a dental membrane is generally manufactured in a rectangular sheet shape, on which the following descriptions are based, the disclosure is not limited thereto, and the dental membrane may be manufactured in a circular, oval, or amorphous shape according to treatment conditions.

The insertion and fixing portion 3 may be provided in at least one portion of the circumference of the shielding portion 2. As illustrated in (a) of FIG. 1, the insertion and fixing portion 3 may be provided at one side of a rectangular shape based on the shielding portion 2 in a rectangular shape, as illustrated in (b) of FIG. 1, the insertion and fixing portion 3 may be provided at two neighboring sides of the rectangular shape, or as illustrated in (d) of FIG. 1, the insertion and fixing portion 3 may be provided at three neighboring sides of the rectangular shape.

Unlike the above, as illustrated in (c) of FIG. 1, the insertion and fixing portions 3 may be arranged to face each other with the shielding portion 2 therebetween and to be connected to the shielding portion 2, or as illustrated in (e) of FIG. 1, the insertion and fixing portion 3 may be provided to surround the shielding portion 2 that is provided at a center portion.

The above structure may vary according to the treatment conditions such as the size, shape, and the like, of the insertion and fixing portion 3 to be inserted between an alveolar bone 5 and a gum 4, which are determined according to the shape of the alveolar bone 5 that is currently left, an area to be regenerated and an amount of a bone grafting material to be inserted, and the like. Accordingly, the structure may be provided in a shape according to each treatment condition.

The shielding portion 2 functions to shield the bone grafting material and the alveolar bone from the outside to prevent infiltration of other tissue cells. In detail, the shielding portion 2 prevents formation of bone tissues as other tissue cells infiltrate between the bone grafting material and the alveolar bone after the grafting surgery of the bone grafting material, thereby stably guiding bone tissue cells.

The insertion and fixing portion 3 is connected to the shielding portion 2, and inserted between the gum 4 (see FIG. 2) and the alveolar bone 5 (see FIG. 2) to fix the shielding portion 2.

However, as the insertion and fixing portion 3 not only fixes the shielding portion 2, but also basically has the above-described shield effect like the shielding portion 2, while performing the same function as the shielding portion 2, the insertion and fixing portion 3 also performs fixing the shielding portion 2 because the insertion and fixing portion 3 has a higher tensile strength than the shielding portion 2.

In detail, while the dental dual-structured membrane 1 including the shielding portion 2 and the insertion and fixing portion 3, as the whole of a membrane sheet having a sheet shape, shields the bone grafting material and the alveolar bone from the outside to prevent infiltration of other tissue cells, the insertion and fixing portion 3 that is a portion having a higher tensile strength is inserted between the gum 4 (see FIG. 2) and the alveolar bone 5 (see FIG. 2) to be firmly fixed therebetween.

Furthermore, the whole of the dental dual-structured membrane 1 may be fixed at a desired position to allow the shielding portion 2 connected to the insertion and fixing portion 3 to be placed at a desired position, and after being fixed, the shielding portion 2 may be maintained without moving at a fixed positon.

Consequently, as the dental dual-structured membrane 1 according to the present inventive concept has a dual-structure including the shielding portion 2 and the insertion and fixing portion 3 having tensile strength different from each other, one sheet shape has an excellent fixing effect, and thus, to fix the dental membrane, an additional treatment, for example, using an additional screw, and the like, is unnecessary, and efforts to install a fixing structure, and the like, on a membrane are unnecessary.

In detail, referring to FIG. 2, after a tooth is extracted in a step (a), in a step (b), in a recess portion where the alveolar bone 5 is destroyed, the insertion and fixing portion 3 (see FIG. 1) of the dental dual-structured membrane 1 according to the present inventive concept is inserted between the alveolar bone 5 that is destroyed and the gum 4 and fixed thereon. Then, in a step (c), the recess portion is filled with a bone grafting material 6, and in a step (d), the dental dual-structured membrane 1 is folded to allow the shielding portion 2 and the bone grafting material 6 to come in contact with each other. A treatment is completed by suturing the gum 4.

In particular, as the insertion and fixing portion 3 having great tensile strength and bending strength is stably placed between the gum 4 and the alveolar bone 5, the dental dual-structured membrane 1 is prevented from freely moving, and thus a manipulation may become easy and treatment convenience may be enhanced.

In addition, as the movement of the dental dual-structured membrane 1 is prevented during a surgery procedure and after the surgery, regeneration may take place as close as possible to designed alveolar bone regeneration during several months of a regeneration period.

The shielding portion 2 and the insertion and fixing portion 3 of the dental dual-structured membrane 1 according to the present inventive concept may include a biodegradable material that is resorbable, and as the biodegradable material is used, after the grafting surgery of a bone grafting material, when bone regeneration is completed, no secondary surgery to remove the membrane is necessary.

The biodegradable material may include a biodegradable polymer selected from among, for example, collagen, fibrinogen, chitosan, gelatin, cellulose, hyaluronic acid, and dextran. Although a case of using collagen is described below, the disclosure is not limited thereto.

The dental dual-structured membrane 1 according to the present inventive concept, which uses a biodegradable polymer as a material, is generally biodegraded after a period of about 6 months, facilitates the bonding and regeneration of the bone grafting material and the existing alveolar bone, and may be safely protected from the outside during a regeneration period.

Although the shielding portion 2 and the insertion and fixing portion 3 of the dental dual-structured membrane 1 according to the present inventive concept are different from each other in the tensile strength due to density difference, the dental dual-structured membrane 1 may be manufactured to have the difference in tensile strength due to a different molecular structure. A method for manufacturing a dental dual-structured membrane, which generates the tensile strength difference, is described below.

Figure 3:
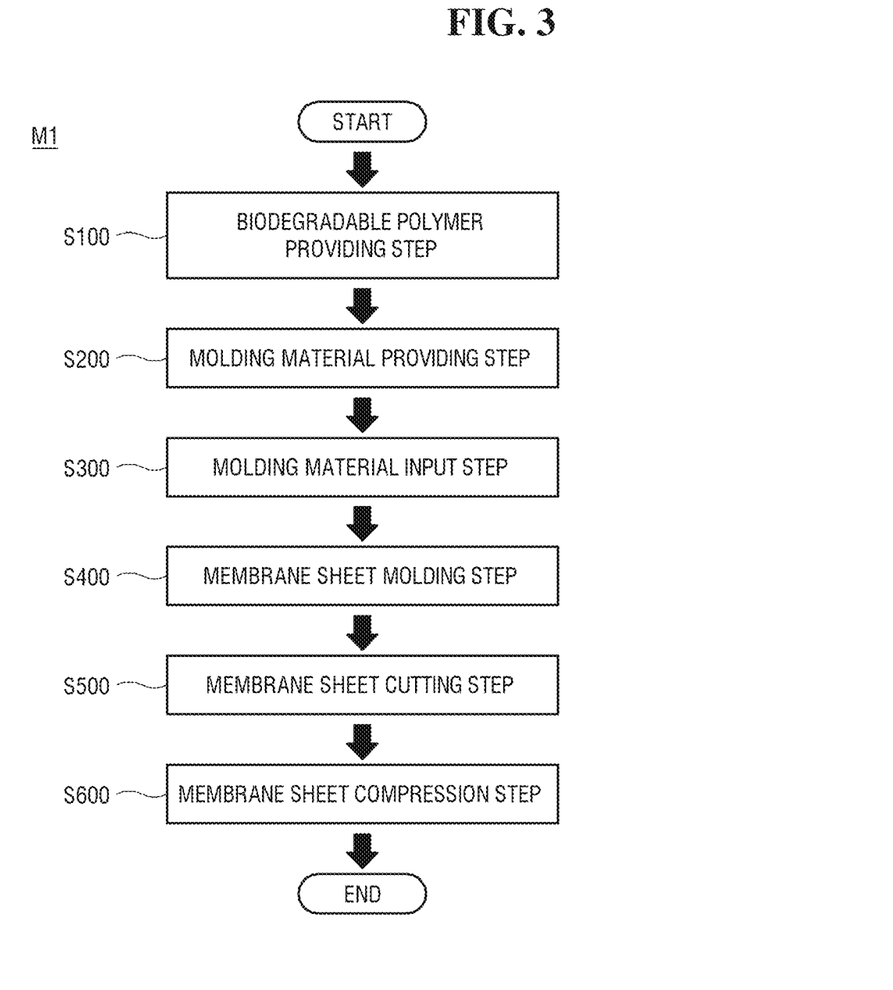
FIG. 3 is a flowchart showing, step-by-step, a method for manufacturing a dental dual-structured membrane according to a first embodiment of the present inventive concept.
Figure 4:
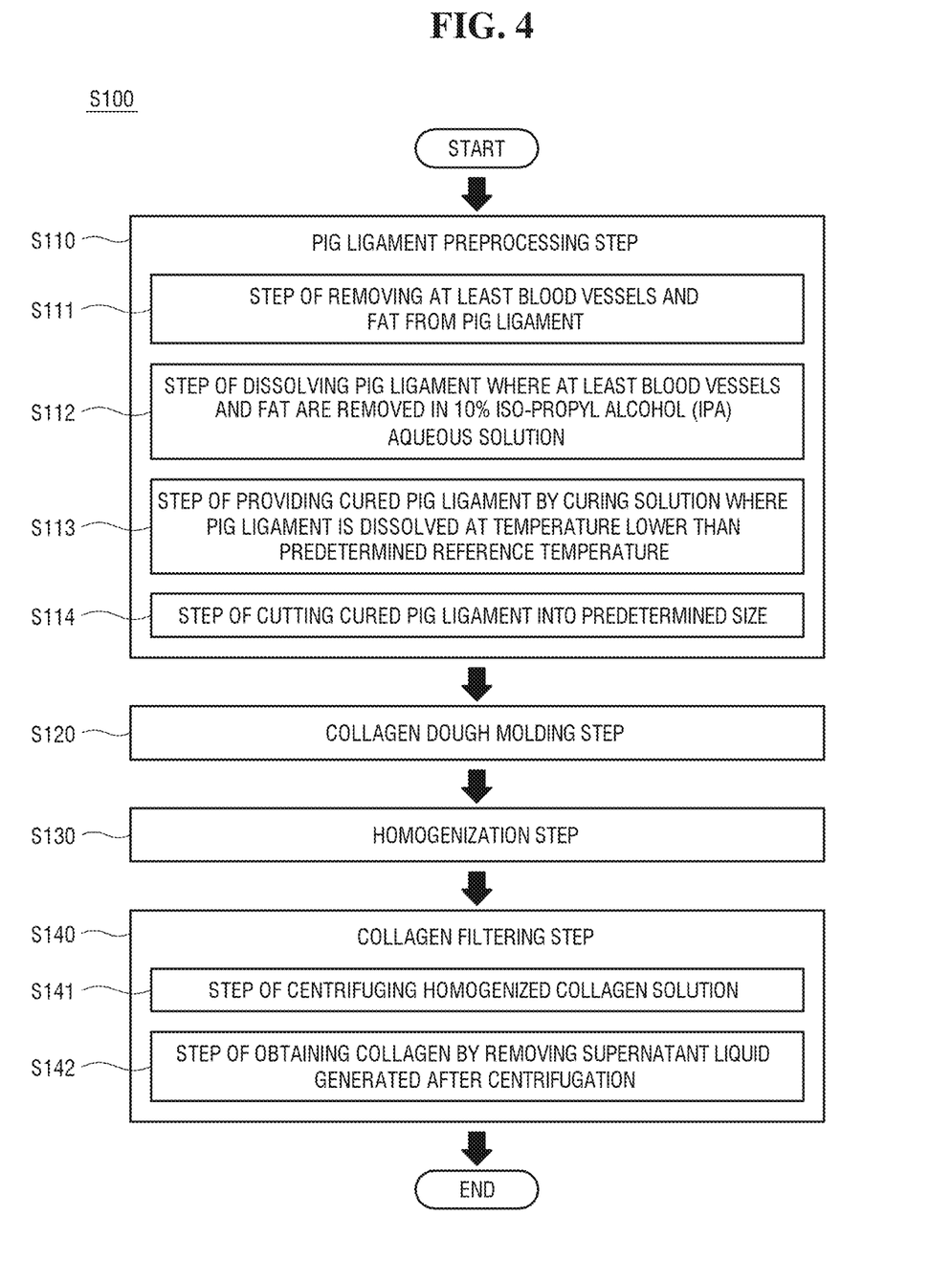
FIG. 4 is a flowchart sequentially showing a collagen providing step of providing porcine-derived collagen, as a biodegradable polymer providing step of FIG. 3.
Figure 5:
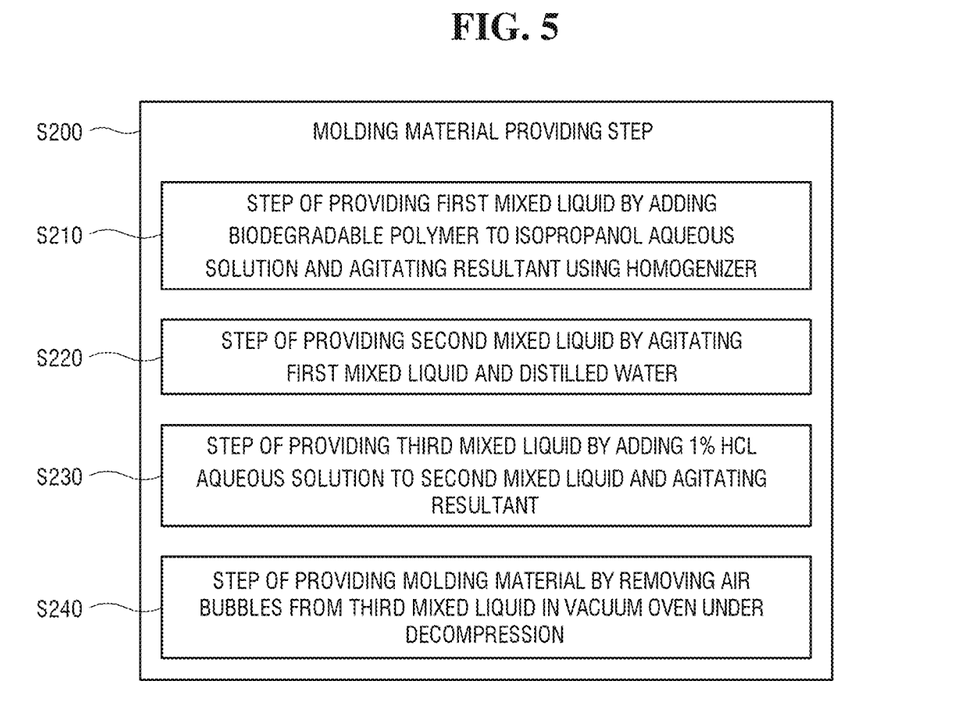
FIG. 5 is a flowchart sequentially showing the molding material providing step of FIG. 3.

FIG. 3 is a flowchart showing, step-by-step, a method for manufacturing a dental dual-structured membrane according to a first embodiment of the present inventive concept. FIG. 4 is a flowchart sequentially showing a collagen providing step of providing porcine-derived collagen, as a biodegradable polymer providing step of FIG. 3. FIG. 5 is a flowchart sequentially showing the molding material providing step of FIG. 3.

As illustrated in detail in FIG. 3, a method M1 for manufacturing a dental dual-structured membrane according to a first embodiment of the present inventive concept is a method for manufacturing the dental dual-structured membrane 1 (see FIG. 1), the dental dual-structured membrane 1 including a the shielding portion 2 (see FIG. 1) that contacts a bone grafting material to prevent infiltration of other tissue cells toward the bone grafting material and an alveolar bone, and the insertion and fixing portion 3 (see FIG. 1) that is connected to the shielding portion 2, has a higher tensile strength than the shielding portion 2, and inserted between the gum 4 (see FIG. 2) and the alveolar bone 5 (see FIG. 2) to fix the shielding portion 2, and the method M1 for manufacturing a dental dual-structured membrane including a biodegradable polymer providing step S100, a molding material providing step S200, a molding material input step S300, a membrane sheet molding step S400, a membrane sheet cutting step S500, and a membrane sheet compression step S600.

First, the biodegradable polymer providing step S100 is a step of providing a biodegradable polymer, and in the first embodiment of the inventive concept, collagen, in particular, porcine-derived collagen, is provided as a biodegradable polymer. As illustrated in detail in FIG. 4, the biodegradable polymer providing step S100 may include a pig ligament preprocessing step S110, a collagen dough molding step S120, a homogenization step S130, and a collagen filtering step S140.

The collagen is one of biodegradable polymers such as collagen, fibrinogen, chitosan, gelatin, cellulose, hyaluronic acid, dextran, and the like. Although a case of using collagen is mainly described in the first embodiment of the inventive concept, the disclosure is not limited thereto, and in addition to collagen, the above-exampled other biodegradable polymers may be used.

Collagen is a main component of connective tissue, as a structural protein that composes tissues and organs of the human body, and refers to an animal fibrous protein composed of about 18 amino acids such as glycine, proline, and the like. For a human, the collagen is a special structure protein that accounts for the most 35% of 5,000 types of proteins that make up the human body.

In particular, the collagen is present in the skin, bones, and tendons, and has a shape in which various amino acids are combined in the form of a polypeptide and twisted in three strands, and its molecular weight is very large to be about 300,000.

There are various types of collagen according to the kind, portion, and type of animals, and the respective collagens have not only different characteristics, but also have different biomolecules or ingredients of composed protein, and the like. Accordingly, collagen that is necessarily suitable for a human body may be used.

According to the first embodiment of the inventive concept, porcine-derived collagen may be provided by using a method of providing porcine-derived collagen, and unlike the above, porcine skin-derived collagen and crosslinked collagen may be provided to use.

The pig ligament preprocessing step S110, which is a step of preprocessing a pig ligament to obtain collagen from the pig ligament, may include a step S111 of removing at least blood vessels and fat from a pig ligament, a step S112 of dissolving the pig ligament, where at least blood vessels and fat are removed, in an iso-propyl alcohol (IPA) aqueous solution, a step S113 of providing a cured pig ligament by curing a solution where the pig ligament is dissolved, at a temperature lower than a predetermined reference temperature, and a step S114 of cutting the cured pig ligament into a predetermined size.

The collagen dough molding step S120, which is step of molding a preprocessed pig ligament into a collagen dough, may include a step of adding the preprocessed pig ligament to a 3% acetic acid aqueous solution where pepsin is dissolved, and mixing the resultant by using a Stephan mixer, a step of providing a first mixture by adding a 3% acetic acid aqueous solution to the mixed solution and agitating the resultant for 5-7 minutes, a step of providing a first dough by removing, by using a press machine, liquid from the first mixture obtained by the agitation, a step of providing a second mixture by adding the first dough to an aqueous solution obtained by dissolving $Na_2HPO_4$ in purified water and agitating the resultant, a step of providing a second dough by removing, by using a press machine, liquid from the second mixture obtained by the agitation, a step of providing a third mixture by adding the second dough to a 15% IPA aqueous solution and agitating the resultant by using a Stephan mixer, and a step of molding a collagen dough by removing, by using a press machine, liquid from the third mixture obtained by the agitation.

In the homogenization step S130, which is a step of dissolving the collagen dough in a solvent to obtain a homogenized collagen solution, a homogenized collagen solution may be obtained by agitating the collagen dough obtained from the collagen dough molding step S120 with a 10% ethanol aqueous solution by using a Stephan mixer, and homogenizing the resultant by using a microfluidizer.

The collagen filtering step S140, which is a step of filtering collagen from a homogenized collagen solution, may include a step S141 of centrifuging the homogenized collagen solution and a step S142 of obtaining collagen by removing a supernatant liquid generated after the centrifugation.

The molding material providing step S200, which is a step of providing a molding material including a biodegradable polymer, as illustrated in detail in FIG. 5, may include a step S210 of providing a first mixed liquid by adding a biodegradable polymer to isopropanol aqueous solution and agitating a resultant using a homogenizer, a step S220 of providing a second mixed liquid by agitating the first mixed liquid and distilled water, a step SS230 of providing a third mixed liquid by adding a 1% HCl aqueous solution to the second mixed liquid and agitating the resultant, and a step S240 of providing a molding material by removing air bubbles from the third mixed liquid in a vacuum oven under decompression.

The molding material input step S300 is a step of inputting a molding material into a sheet type mold for molding the molding material in the form of a sheet, the membrane sheet molding step S400 is a step of molding the molding material input into the sheet type mold into a membrane sheet by drying the molding material, and the membrane sheet cutting step S500 is a step of cutting the membrane sheet in a predetermined size.

The membrane sheet compression step S600 is a step of compressing a part of the membrane sheet to provide the insertion and fixing portion 3 (see FIG. 1) having a reinforced tensile strength and the shielding portion 2 (see FIG. 1) that is the other part of the membrane sheet.

As a part of the membrane sheet is compressed, a density difference is generated between a compressed part and an uncompressed part of the membrane sheet, and thus a difference is generated in the tensile strength.

Accordingly, referring to FIG. 1, in the membrane sheet, the uncompressed part becomes the shielding portion 2 having a certain tensile strength, and the compressed part becomes the insertion and fixing portion 3 having a higher tensile strength than the shielding portion 2.

Consequently, according to the method M1 for manufacturing a dental dual-structured membrane according to the first embodiment of the inventive concept, as the difference in tensile strength occurs in the step of molding the membrane sheet having the same tensile strength, as a whole, and then compressing a part to be the insertion and fixing portion 3, the membrane sheet is divided into the shielding portion 2 and the insertion and fixing portion 3. The tensile strength is reinforced due to the density difference that partially occurs by compressing a part of the membrane sheet.

Table 1 shows a test result of a difference in tensile strength between the shielding portion and the insertion and fixing portion of the dental dual-structured membrane manufactured by the method M1 for manufacturing a dental dual-structured membrane according to the first embodiment of the inventive concept.

TABLE 1

|  | Shielding portion | Insertion and fixing portion |
| --- | --- | --- |
| Tensile strength (mpa) | 3.71 | 4.52 |

As such, according to the present embodiment, as the dental dual-structured membrane has a dual-structure in which at least one portion of a dental membrane has a higher tensile strength than the other portion thereof, the dental dual-structured membrane, which may be accurately fixed at a desired position and may be prevented from moving away from the fixed position, may be simply and efficiently manufactured.

Figure 6:
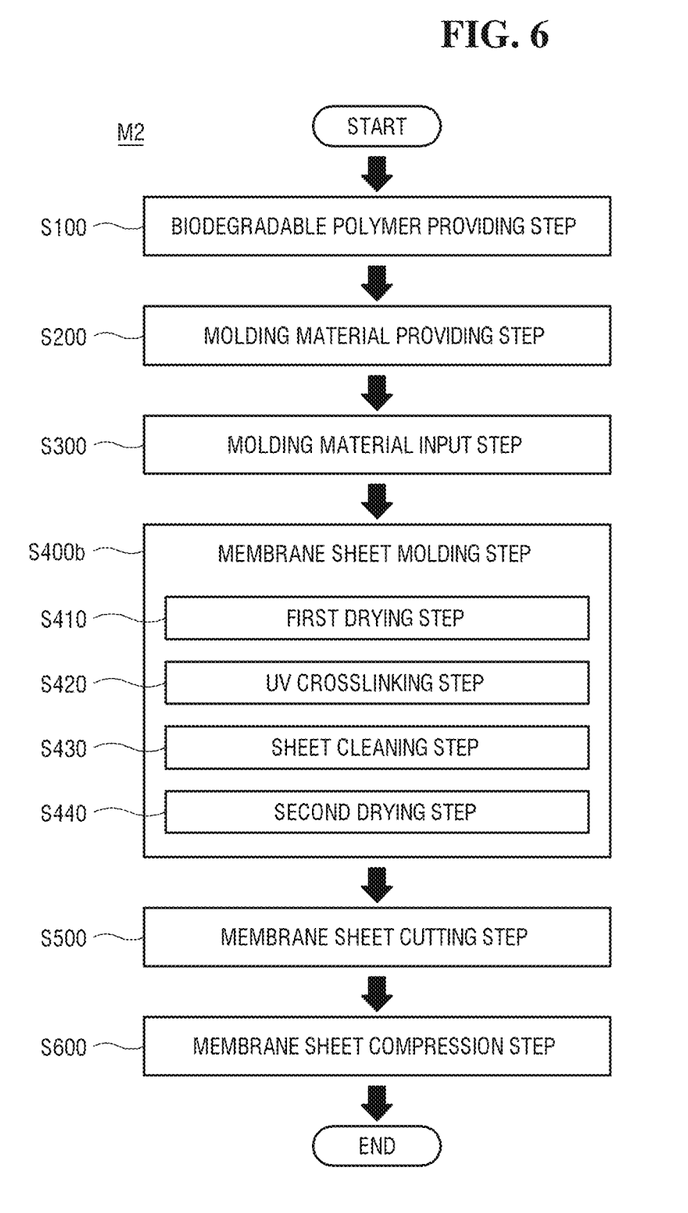
FIG. 6 is a flowchart showing, step-by-step, a method for manufacturing a dental dual-structured membrane according to a second embodiment of the present inventive concept.

FIG. 6 is a flowchart showing, step-by-step, a method for manufacturing a dental dual-structured membrane according to a second embodiment of the present inventive concept.

According to a method M2 for manufacturing a dental dual-structured membrane according to a second embodiment of the present inventive concept, compared to the first embodiment, as there is a difference in that a separate step of reinforcing a tensile strength is performed in a membrane sheet molding step S400b, the membrane sheet molding step S400b is mainly described.

The membrane sheet molding step S400b, as illustrated in detail in FIG. 6, may include a first drying step S410, a UV crosslinking step S420, a sheet cleaning step S430, and a second drying step S440.

The first drying step S410 is a step of providing a first dry sheet by drying, in an oven, a sheet type mold into which a molding material is input, through which a liquid molding material may have a sheet shape.

The UV crosslinking step S420 is a step of providing a crosslinked sheet with a reinforced tensile strength by crosslinking a biodegradable polymer by irradiating ultraviolet (UV) light to a predetermined position of a first dry sheet where the insertion and fixing portion is to be provided.

In the UV crosslinking step S420, a part of the first dry sheet, where the shielding portion is to be formed, is covered with aluminum foil and put into a UV-crosslinking chamber to be irradiated by UV light for a certain time.

Accordingly, as the part covered with the aluminum foil is not irradiated by the UV light, the part is not changed at all. However, a part onto which the UV light is irradiated is crosslinked by a crosslinking reaction, and thus a molecular structure becomes denser and the tensile strength may be reinforced.

Consequently, the part covered with aluminum foil becomes the shielding portion where no change occurs in tensile strength, and the part irradiated by the UV light has a dense molecular structure by crosslinking so that tensile strength increases and the part becomes the insertion and fixing portion.

The sheet cleaning step S430 is a step of cleaning the crosslinked sheet, and may include a step of putting the crosslinked sheet in a tray containing a phosphate buffered saline (PBS) liquid and shaking the tray, and a step of removing the PBS liquid and cleaning the crosslinked sheet using distilled water until the pH reaches 7.0 to 8.0.

Through the cleaning step, impurities or low molecular weight material included in the crosslinked sheet may be removed.

The second drying step S440 is a step of molding the cleaned crosslinked sheet into a membrane sheet by freezing and drying the cleaned crosslinked sheet at a temperature lower than a predetermined reference temperature.

While all parts of the membrane sheet formed through the membrane sheet molding step S400 in the first embodiment have the same tensile strength, the membrane sheet formed through the membrane sheet molding step S400b in the second embodiment has a part having a different tensile strength so as to be molded in a state in which the shielding portion and the insertion and fixing portion are divided.

Thereafter, the tensile strength is reinforced again by undergoing the membrane sheet compression step S600 that is the same as in the first embodiment.

Consequently, according to the method M2 for manufacturing a dental dual-structured membrane according to the second embodiment of the present inventive concept, the tensile strength is increased as a part to be the insertion and fixing portion primarily undergoes the UV crosslinking step S420 so as to have a dense molecular structure by crosslinking, and the tensile strength is reinforced again due to the density difference that partially occurs as the part secondarily undergoes the compression step.

Table 2 shows a test result of a difference in tensile strength between the shielding portion and the insertion and fixing portion of the dental dual-structured membrane manufactured by the method M2 for manufacturing a dental dual-structured membrane according to the second embodiment of the inventive concept.

TABLE 2

|  | Shielding portion | Insertion and fixing portion |
| --- | --- | --- |
| Tensile strength (mpa) | 3.71 | 8.23 |

As such, according to the present embodiment, by undergoing the two-time tensile strength reinforcement step, compared to the first embodiment, the insertion and fixing portion may have a higher tensile strength.

Figure 7:
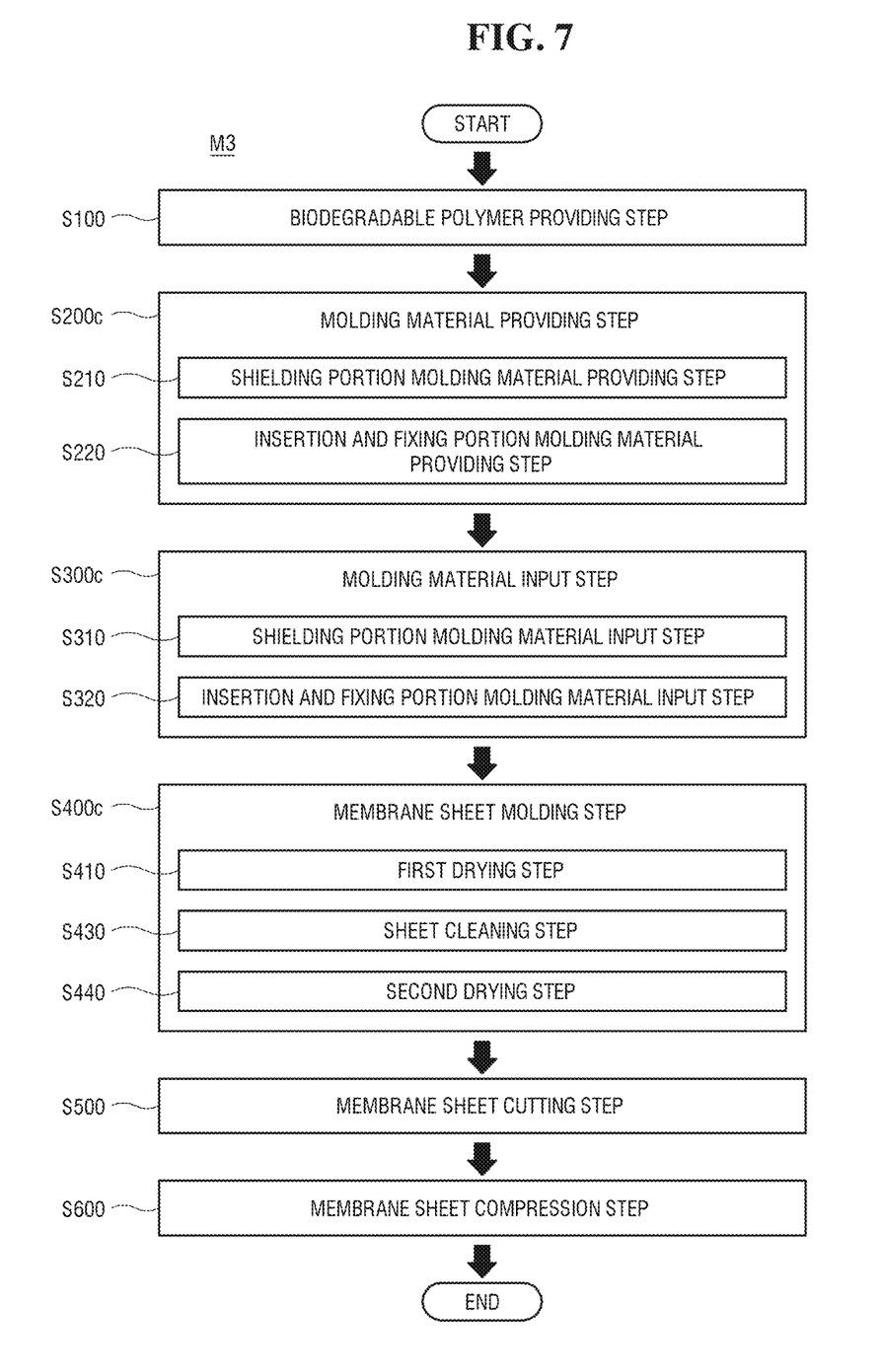
FIG. 7 is a flowchart showing, step-by-step, a method for manufacturing a dental dual-structured membrane according to a third embodiment of the present inventive concept.

FIG. 7 is a flowchart showing, step-by-step, a method for manufacturing a dental dual-structured membrane according to a third embodiment of the present inventive concept.

According to a method M3 for manufacturing a dental dual-structured membrane according to a third embodiment of the present inventive concept, compared to the first and second embodiments, while there is differences in a molding material providing step S200c, a the molding material input step S300c, and a membrane sheet molding step S400c, the other steps are the same. Accordingly, only the difference steps are mainly described.

In the molding material providing step S200c, a molding material is provided separately as a shielding portion molding material for forming a shielding portion and insertion and an insertion and fixing portion molding material for forming a fixing portion.

As the shielding portion molding material and the insertion and fixing portion molding material are separately provided, in the step of forming a membrane sheet according to a difference of a molding material, even without performing a separate process as in the second embodiment, the tensile strength of the shielding portion and the insertion and fixing portion may be differently set by the forming of a membrane sheet only.

The difference of a molding material may include different constituent elements, and in the present embodiment, the difference may be simply obtained as the shielding portion molding material is provided to include a larger amount of distilled water than the insertion and fixing portion molding material. However, the disclosure is not limited thereto, and by differentiating the constituent elements of a molding material, the difference in tensile strength may be set to be further great.

Next, in the molding material input step S300c, the shielding portion molding material is input into one predetermined area of a sheet type mold where the shielding portion is to be formed, and the insertion and fixing portion molding material is input into the other predetermined area of the sheet type mold where the insertion and fixing portion is to be formed.

As such, by providing separate molding materials and separately inputting and drying the separate molding materials in specific parts of the sheet type mold, a membrane sheet including a shielding portion and an insertion and fixing portion having tensile strength different from each other may be formed.

The membrane sheet molding step S400c of the third embodiment, as illustrated in detail in FIG. 7, may omit the UV crosslinking step S420 of the second embodiment and may include the first drying step S410, the sheet cleaning step S430, and the second drying step S440.

After the membrane sheet molding step S400c, the membrane sheet compression step S600 that is the same as one in the first embodiment is performed so that the tensile strength is reinforced again.

Consequently, according to the method M3 for manufacturing a dental dual-structured membrane according to the third embodiment of the present inventive concept, by providing separate molding materials and separately inputting and drying the separate molding materials in specific parts of a sheet type mold, a part to be the insertion and fixing portion primarily has a higher tensile strength than the shielding portion, and secondarily, through the compression step, the tensile strength is reinforced again due to the density difference that partially occurs.

Table 3 shows a test result of a difference in tensile strength between the shielding portion and the insertion and fixing portion of the dental dual-structured membrane manufactured by the method M3 for manufacturing a dental dual-structured membrane according to the third embodiment of the inventive concept.

TABLE 3

|  | Shielding portion | Insertion and fixing portion |
|---|---|---|
| Tensile strength (mpa) | 3.71 | 6.45 |

As such, according to the present embodiment, the insertion and fixing portion may have a quite high tensile strength compared to the first embodiment by undergoing the tensile strength reinforcement step twice.

Figure 8:
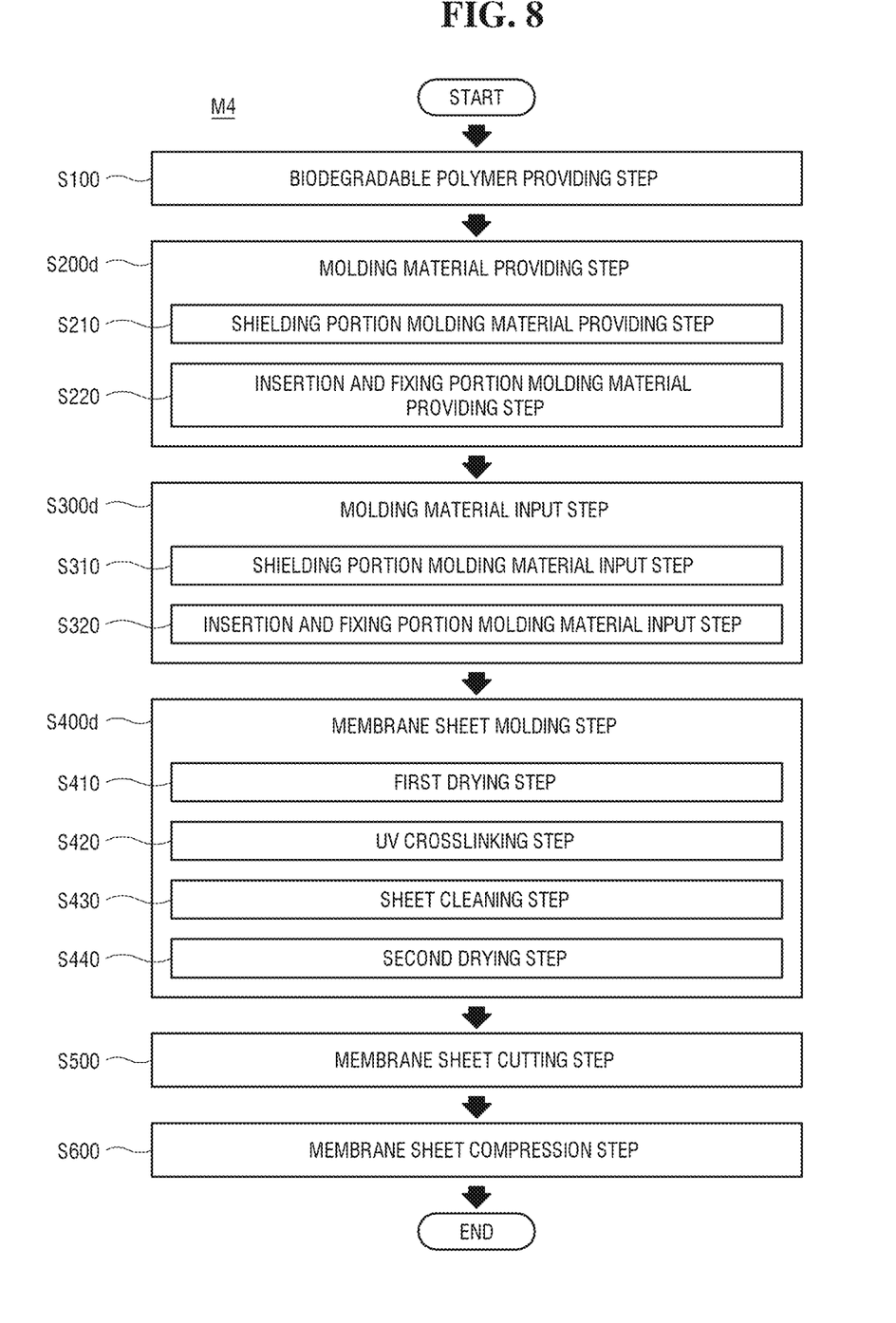
FIG. 8 is a flowchart showing, step-by-step, a method for manufacturing a dental dual-structured membrane according to a fourth embodiment of the present inventive concept.

FIG. 8 is a flowchart showing, step-by-step, a method for manufacturing a dental dual-structured membrane according to a fourth embodiment of the present inventive concept.

According to a method M4 for manufacturing a dental dual-structured membrane a fourth embodiment of the present inventive concept, the characteristics of the third embodiment of separately providing the shielding portion molding material and the insertion and fixing portion molding material and inputting the shielding portion molding material and the insertion and fixing portion molding material into the sheet type mold at different positions, the characteristics of the second embodiment including the UV crosslinking step S420, and the characteristics of the first embodiment of reinforcing the tensile strength due to the density difference that partially occurs through the compression step are all included and sequentially performed.

Consequently, according to the method M4 for manufacturing a dental dual-structured membrane according to the fourth embodiment of the present inventive concept, by providing separate molding materials and separately inputting and drying the separate molding materials in specific parts of a sheet type mold, a part to be the insertion and fixing portion primarily has a higher tensile strength than the shielding portion, and secondarily, a dense molecular structure is formed by crosslinking through the UV crosslinking step S420 so that the tensile strength is increased again, and thirdly, through the compression step, the tensile strength is reinforced again due to the density difference that partially occurs.

Accordingly, the tensile strength of the insertion and fixing portion may be further reinforced compared to the previous embodiments.

As such, while this present inventive concept has been particularly shown and described with reference to preferred embodiments thereof, it will be understood by those of ordinary skill in the art that various changes in form and details may be made therein without departing from the spirit and scope of the inventive concept as defined by the appended claims. The preferred embodiments should be considered in descriptive sense only and not for purposes of limitation. Therefore, the scope of the inventive concept is defined not by the detailed description of the inventive concept but by the appended claims, and all differences within the scope will be construed as being included in the inventive concept.

INDUSTRIAL APPLICABILITY

The present inventive concept may be used for a medical industry, particularly for a dental medical industry.

The invention claimed is:
1. A dental dual-structured membrane comprising:
a shielding portion for shielding a bone grafting material and an alveolar bone from outside to prevent infiltration of other tissue cells; and an insertion and fixing portion connected to the shielding portion and inserted between a gum and the alveolar bone to fix the shielding portion,
wherein the insertion and fixing portion has a higher tensile strength than the shielding portion.

2. The dental dual-structured membrane of claim 1, wherein the insertion and fixing portion is provided at at least one portion of a circumference of the shielding portion.

3. The dental dual-structured membrane of claim 2, wherein the insertion and fixing portions are arranged to face each other with the shielding portion between and to be connected to the shielding portion.

4. The dental dual-structured membrane of claim 1, wherein the shielding portion and the insertion and fixing portion each comprise a biodegradable material.

5. The dental dual-structured membrane of claim 1, wherein the shielding portion and the insertion and fixing portion have a difference in tensile strength due to a density difference.

6. The dental dual-structured membrane of claim 1, wherein the shielding portion and the insertion and fixing portion have a difference in tensile strength due to a different molecular structure.

7. A method for manufacturing a dental dual-structured membrane, the dental dual-structured membrane comprising a shielding portion in contact with a bone grafting material to prevent infiltration of other tissue cells toward a bone grafting material and an alveolar bone, and an insertion and fixing portion connected to the shielding portion, having a higher tensile strength than the shielding portion, and inserted between a gum and the alveolar bone to fix the shielding portion, the method comprising:
a biodegradable polymer providing step of providing a biodegradable polymer;
a molding material providing step of providing a molding material comprising the biodegradable polymer;
a molding material input step of inputting the molding material into a sheet type mold to mold the molding material in a form of a sheet;
a membrane sheet molding step of molding the molding material input into the sheet type mold in a membrane sheet by drying the molding material; and
a membrane sheet compression step of compressing a part of the membrane sheet to provide the insertion and fixing portion having a reinforced tensile strength and the shielding portion that is the other part of the membrane sheet.

8. The method of claim 7, further comprising, after the membrane sheet molding step, cutting the membrane sheet in a predetermined size.

9. The method of claim 7, wherein the molding material providing step comprises:
a step of providing a first mixed liquid by adding the biodegradable polymer to an isopropanol aqueous solution and agitating a resultant using a homogenizer;
a step of providing a second mixed liquid by agitating the first mixed liquid and distilled water;
a step of providing a third mixed liquid by adding a 1% HCl aqueous solution to the second mixed liquid and agitating a resultant; and
a step of providing a molding material by removing air bubbles from the third mixed liquid in a vacuum oven under decompression.

10. The method of claim 9, wherein the membrane sheet molding step comprises:
a first drying step of providing a first dry sheet by drying, in an oven, a sheet type mold into which the molding material is input;
a sheet cleaning step of cleaning the first dry sheet; and
a second drying step of molding a cleaned first dry sheet into a membrane sheet by freezing and drying the cleaned first dry sheet at a temperature lower than a predetermined reference temperature.

11. The method of claim 10, wherein the sheet cleaning step comprises:
a step of putting the first dry sheet in a tray containing a phosphate buffered saline (PBS) liquid and shaking the tray; and
a step of removing the PBS liquid and cleaning the first dry sheet using distilled water until pH reaches 7.0 to 8.0.

12. The method of claim 10, wherein the membrane sheet molding step further comprises, after the first drying step, an ultraviolet (UV) crosslinking step of providing a crosslinked sheet to reinforce tensile strength by crosslinking of the biodegradable polymer, by irradiating UV light to a predetermined position of the first dry sheet where the insertion and fixing portion is to be provided, and
wherein, in the sheet cleaning step, the crosslinked sheet is cleaned.

13. The method of claim 9, wherein the molding material comprises:
a shielding portion molding material for forming the shielding portion; and
an insertion and fixing portion molding material for forming the insertion and fixing portion.

14. The method of claim 13, wherein the shielding portion molding material is provided to include a larger amount of distilled water than the insertion and fixing portion molding material.

15. The method of claim 13, wherein, in the molding material input step, the shielding portion molding material is input into one predetermined area of the sheet type mold where the shielding portion is to be formed, and the insertion and fixing portion molding material is input into another predetermined area of the sheet type mold where the insertion and fixing portion is to be formed.

16. The method of claim 7, wherein the biodegradable polymer comprises collagen, the collagen comprising porcine-derived collagen, and
the biodegradable polymer providing step is a collagen providing step of providing the collagen, the collagen providing step comprises:
a pig ligament preprocessing step of preprocessing a pig ligament to obtain collagen from the pig ligament;
a collagen dough molding step of molding a preprocessed pig ligament into a collagen dough;
a homogenization step of dissolving the collagen dough in a solvent to obtain a homogenized collagen solution; and
a collagen filtering step of filtering collagen from a homogenized collagen solution.

* * * * *